(12) United States Patent
Buchter et al.

(10) Patent No.: US 10,234,396 B1
(45) Date of Patent: Mar. 19, 2019

(54) DEVICE FOR ANALYZING THE MATERIAL COMPOSITION OF A SAMPLE VIA PLASMA SPECTRUM ANALYSIS

(71) Applicant: Rigaku Analytical Devices, Inc., Wilmington, MA (US)

(72) Inventors: Scott Charles Buchter, Espoo (FI); Michael Anthony Damento, Tucson, AZ (US); Stanislaw Piorek, Hillsborough, NJ (US)

(73) Assignee: RIGAKU RAMAN TECHNOLOGIES, INC., Wilmington, MA (US)

( * ) Notice: Subject to any disclaimer, the term of this patent is extended or adjusted under 35 U.S.C. 154(b) by 0 days.

(21) Appl. No.: 16/130,563

(22) Filed: Sep. 13, 2018

(51) Int. Cl.
| | |
|---|---|
| *G01N 21/71* | (2006.01) |
| *G02B 27/09* | (2006.01) |
| *G01J 3/28* | (2006.01) |
| *G01N 21/01* | (2006.01) |
| *G01N 21/47* | (2006.01) |

(52) U.S. Cl.
CPC .............. *G01N 21/718* (2013.01); *G01J 3/28* (2013.01); *G01N 21/01* (2013.01); *G01N 21/4788* (2013.01); *G02B 27/0944* (2013.01)

(58) Field of Classification Search
CPC .. G01N 21/718; G01N 21/01; G01N 21/4788; G01J 3/28; G01J 3/00; G02B 27/0944; G02B 6/00; G02B 6/26; G03B 27/54; G03B 27/42; G03F 9/00
See application file for complete search history.

(56) References Cited

U.S. PATENT DOCUMENTS

2009/0190127 A1 * 7/2009 Kojima ..................... G01J 3/02
356/328

* cited by examiner

*Primary Examiner* — Jamil Ahmed
(74) *Attorney, Agent, or Firm* — Brinks Gilson & Lione

(57) ABSTRACT

A device for analyzing the material composition of a sample via plasma spectrum analysis includes a laser assembly configured to emit a beam for plasma spectrum analysis and an optical assembly configured to direct the beam towards a target for plasma spectrum analysis of the target. The optical assembly is configured to collect a plasma emitted light emitted from a plasma and provide the plasma emitted light to a dispersion module. The dispersion module includes a first and second diffraction gratings. The first diffraction grating and second diffraction grating are positioned within the dispersion module such that light received from the optical assembly contacts the first diffraction grating at least two times before being directed out of the dispersion module.

11 Claims, 5 Drawing Sheets

DEVICE FOR ANALYZING THE MATERIAL COMPOSITION OF A SAMPLE VIA PLASMA SPECTRUM ANALYSIS

BACKGROUND

1. Field of the Invention

The present invention generally relates to laser-induced breakdown spectroscopy systems.

2. Description of Related Art

Laser-induced breakdown spectroscopy ("LIBS") is a type of atomic emission spectroscopy which uses a highly energetic laser pulse as the excitation source. The laser is focused to form a plasma, which atomizes and excites samples. In principle, LIBS can analyze any matter regardless of its physical state, be it solid, liquid, or gas. Because all elements emit light of characteristic frequencies when excited to sufficiently high temperatures, LIBS can detect all elements, limited only by the power of the laser beam utilized as well as the sensitivity and wavelength range of the spectrograph and detector.

If the constituents of a material to be analyzed are known, LIBS may be used to evaluate the relative abundance of each constituent element or to monitor the presence of impurities. In practice, detection limits are a function of a) the plasma excitation temperature, b) the light collection window, and c) the line strength of the viewed transition. LIBS makes use of optical emission spectrometry and is to this extent very similar to arc/spark emission spectroscopy.

LIBS operate by focusing the laser beam onto a small area at the surface of the specimen When the laser beam is discharged it ablates a very small amount of material, in the range of nanograms to picograms, which generates a plasma plume with temperatures in excess of 100,000 K. During data collection, typically after local thermodynamic equilibrium is established, plasma temperatures range from 5,000-20,000 K. At the high temperatures during the early plasma, the ablated material dissociates (breaks down) into excited ionic and atomic species. During this time, the plasma emits a continuum of radiation which does not contain any useful information about the species present, but within a very small timeframe the plasma expands at supersonic velocities and cools. At this point, the characteristic atomic emission lines of the elements can be observed.

SUMMARY

A device for analyzing the material composition of a sample via plasma spectrum analysis may include a laser assembly configured to emit a beam for plasma spectrum analysis and an optical assembly configured to direct the beam towards a target for plasma spectrum analysis of the target. The optical assembly may be configured to collect a plasma emitted light emitted from a plasma and provide the plasma emitted light to a dispersion module.

The dispersion module may include a first diffraction grating configured such that plasma emitted light from the optical assembly is diffracted by the first diffraction grating. The dispersion module may also include a second diffraction grating such that light diffracted by the first diffraction grating would also be diffracted by the second diffraction grating The first diffraction grating and second diffraction grating are positioned within the dispersion module such that light received from the optical assembly contacts the first diffraction grating at least two times before being directed out of the dispersion module.

Further objects, features, and advantages of this invention will become readily apparent to persons skilled in the art after a review of the following description, with reference to the drawings and claims that are appended to and form a part of this specification.

DETAILED DESCRIPTION

Figure 1:
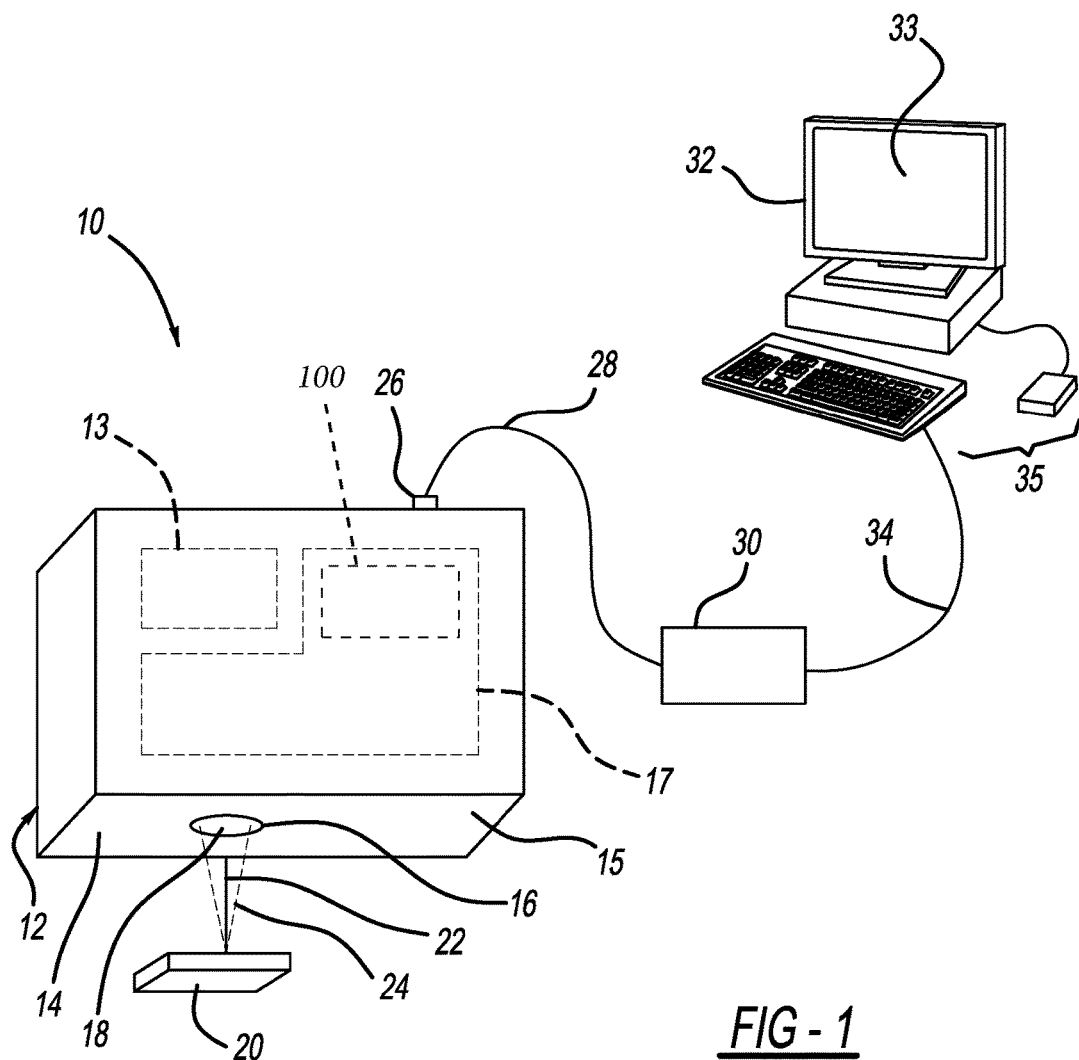
FIG. 1 illustrates a system for analyzing the material composition of a sample by spectrum analysis having a dispersion module.

Referring to FIG. 1, a system 10 for analyzing the material composition of a sample 20 by spectrum analysis is shown. As its primary components, the system 10 includes a device 12 for analyzing the material composition of the sample 20. The device 12 may include a housing 14 which may enclose a number of components that will be described in FIG. 2 and later in this description. For example, the housing 14 may include a laser assembly 13 for producing a laser beam 22 and an optical assembly 17 for directing a laser beam 22 to the sample 20. In addition, the optical assembly 17 may function to direct plasma emitted light 24 to a spectrometer 30 via an optical fiber 28.

The device 12 has two primary functions. The device 12 provides beam shaping and delivery for the laser beam 22 and also efficiently collects the plasma emitted light 24 from the plasma for delivery to the spectrometer 30. The laser beam 22 may be a single mode laser beam having a focused diameter of 20 microns on the sample 20 in order to generate a strong plasma plume. The working distance may be around or greater than 10 mm.

The optical assembly 17 may also include a dispersion module 100. The dispersion module 100 may be part of the optical assembly 17 or may be separate from the optical assembly 17. The dispersion module 100 will be described in more detail later in this detailed description. The dispersion module 100 allows for a much greater resolution in a far more compact device than presently available. This allows for, for example, quick and accurate measurement of an amount of carbon within sample 20. The dispersion module 100 may be located, as stated previously, within the device 12 or could be alternatively, located within the spectrometer 30. In either case, the dispersion module 100 is to receive emitted light 24 from the plasma and then directs the submitted light to a detector.

A wall portion 15 of the housing 14 may have an opening 16 formed therein. The opening 16 may contain a window 18. The window 18 may be a transparent window allowing for the transmission of light to and from the device 12, such as the laser beam 22 and the plasma emitted light 24. The housing 14 may be hermetically sealed and may be filled with an inert gas.

As stated before, the device 12 is configured to emit a laser beam 22 towards the sample 20. When the laser beam 22 strikes the sample 20, a plasma plume is formed and plasma emitted light 24 is reflected back to the window 18. The plasma emitted light 24 is redirected to the spectrometer 30 via the optical fiber 28. The fiber adapter 26 optically directs the plasma emitted light 24 to the optical fiber 28. The optical fiber 28, in turn, directs the plasma emitted light 24 to a spectrometer 30.

The dispersion module 100, in a situation as shown wherein the dispersion module is located within the device 12, will first receive the plasma emitted light 24 and direct this light to the spectrometer 30 via the optical fiber 28. Alternatively, the dispersion module 100 may be located within the spectrometer 30 and may first receive plasma emitted light 24 from the optical fiber 28 before providing it to a detector, as will be described later in this detailed description section.

The spectrometer 30 may perform a number of different spectral analyses of the plasma emitted light 24 and converts these optical signals into electrical signals that are provided to digital analyzer 32.

The spectrometer 30 may include a monochromator (scanning) or a polychromator (non-scanning) and a photomultiplier or CCD (charge coupled device) detector, respectively. The spectrometer 30 collects electromagnetic radiation over the widest wavelength range possible, maximizing the number of emission lines detected for each particular element. The response of the spectrometer 30 may be from 1100 nm (near infrared) to 170 nm (deep ultraviolet).

The electrical signals generated by the spectrometer 30 may be provided to the digital analyzer 32 by a cable 34. However, it should be understood that any one of a number of different methodologies utilized to transmit digital data from separate devices may be employed. For example, the digital analyzer 32 may utilize a wireless protocol to communicate with the spectrometer 30. The digital analyzer 32 may be a dedicated device having an output device 33 and one or more input devices 35. The output device 33 may be a display, while the input device 35 may be a keyboard and/or a mouse.

Figure 2A:
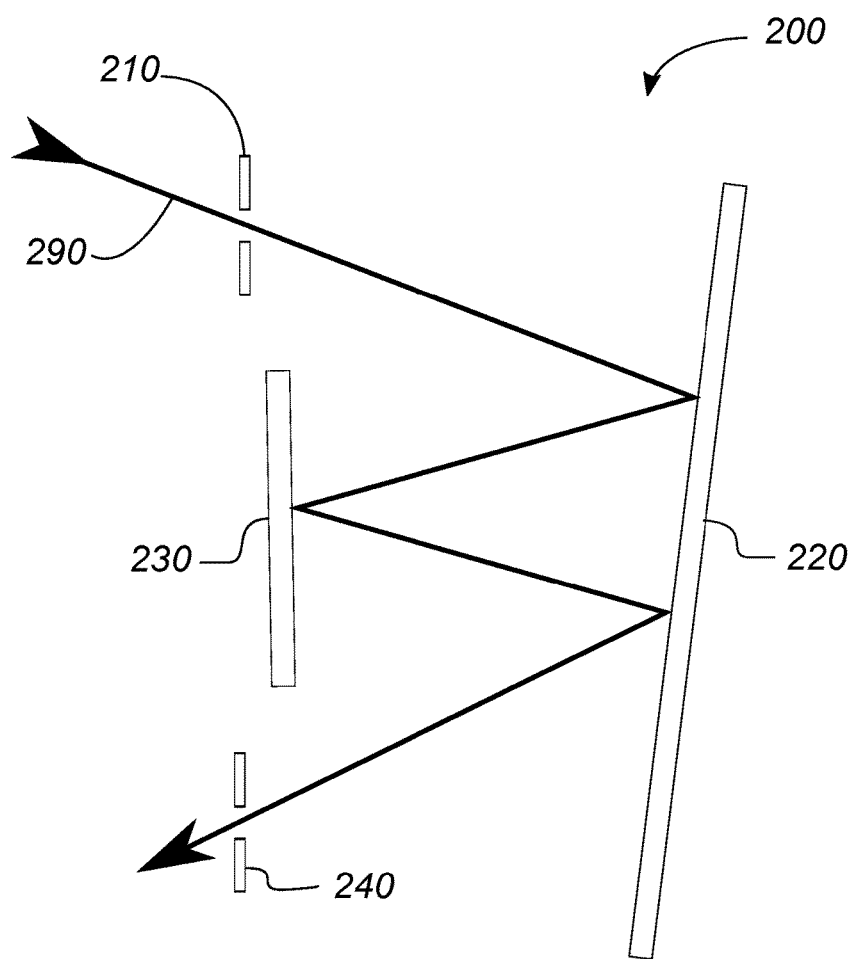
FIGS. 2A and 2B illustrate examples of the dispersion module.
Figure 2B:
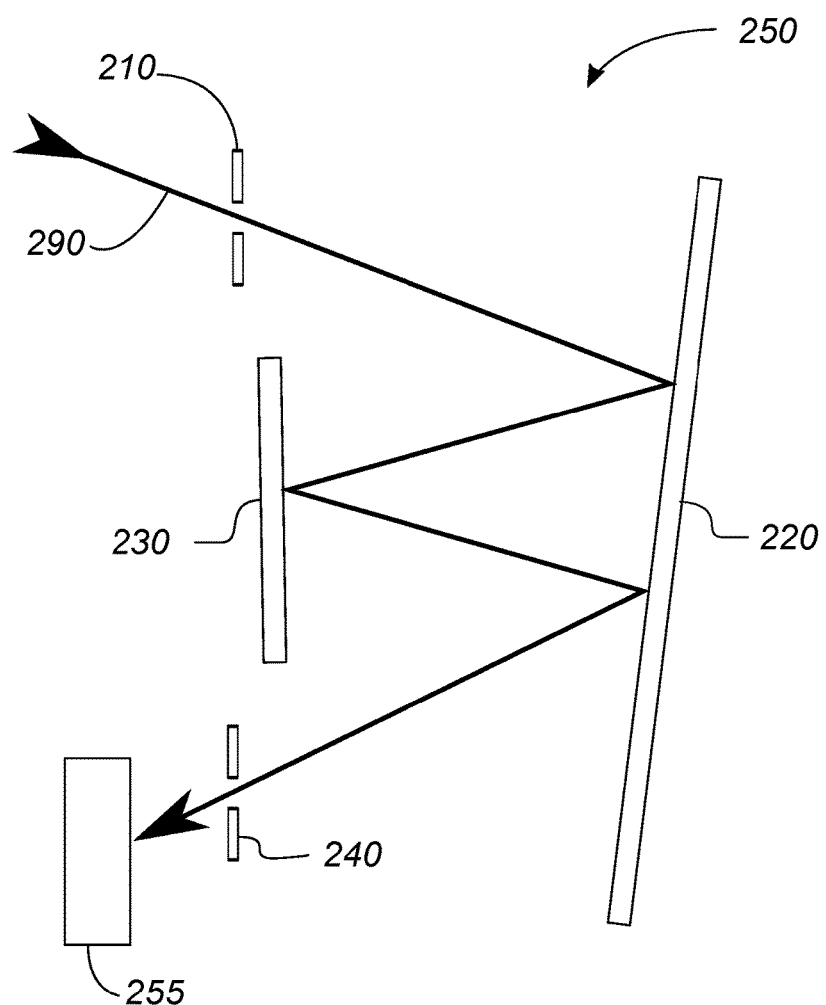

FIGS. 2A and 2B illustrate an example of a dispersion module 200 and 250 for a spectrometer, respectively. Here, the dispersion module 100 of FIG. 1 is referred to as dispersion module 200. As shown, the dispersion module 200 comprises: an entrance 210 for receiving light; a first diffraction grating 220 affixed within the dispersion module such that light received at the entrance 210 would be diffracted by the first diffraction grating 220; a second diffraction grating 230 affixed within the dispersion module 200 relative to the first diffraction grating 220 such that light diffracted by the first diffraction grating 220 would also be diffracted by the second diffraction grating 230; and an exit 240 for transmitting light out of the module after it has been diffracted by the first and second diffraction gratings. As seen, the first diffraction grating 220 and second diffraction grating 230 are affixed within the dispersion module 200 such that light 290 (such as the plasma in emitted light 24 of FIG. 1) received at the entrance 210 would contact the first diffraction grating 220 at least two times before being directed to the exit.

In at least some dispersion modules, the first diffraction grating 220 and second diffraction grating 230 are reflective diffraction gratings. Certain modules employ a transmission diffraction grating as either the first or second diffraction grating. Some modules employ a transmission diffraction grating as both the first and second diffraction grating. In certain modules at least one of the first and second diffraction grating is a blazed diffraction grating, for example, a blazed diffraction grating optimized for a wavelength between 150 nm and 250 nm and more specifically between 175 nm and 200 nm.

Within certain dispersion modules, the first reflective diffraction grating 220 and second reflective diffraction grating 230 are movably affixed within the dispersion module 200 to provide for tuning of the module. The first reflective diffraction grating 220 and/or second reflective diffraction grating 230 may be transmissive diffraction gratings.

Some dispersion modules according to the present invention have a dispersion rating of at least 20 mrad/nm, preferably X mrad/nm and most preferably Y mrad/nm.

Certain dispersion modules according to the present invention employ a lens as the entrance to the module. Some modules employ a slit as the entrance. Within certain dispersion modules, there is a substantially parallel beam of light, caused by a slit or lens at the entrance, upon contact with the first diffraction grating.

As also seen in FIG. 2A at least some dispersion modules according to the present invention provide for an entrance and exit on the same side of the module. This arrangement provides for a more compact module which may be employed in a wide array of applications.

As shown, dispersion modules according to the present invention allow for multiple reflections per grating. For each reflection on a grating that gratings lines per length is applied. In other words, reflecting twice off of a grating having 3600 lines/mm gives an effective grating of 7200 lines/mm. In this fashion arranging two gratings to reflect light five times each would result in an effective grating of 36000 lines/mm. (5*2*3600 lines/mm) In this fashion dispersion modules according to the present invention provide for much greater effective lines per mm.

Dispersion modules according to the present invention allow for much greater resolution while maintaining sufficient efficiency to provide accurate readings and consistent use of light exiting the modules. Within at least some applications only 1% of light need be retained for accurate measurement. As such at 90% efficiency per reflection by a dispersion grating and even 10 reflections at 90% per reflection would result in roughly 35% of light remaining, 85% efficiency would leave 20%, even 60% would leave 0.6%. Certain applications would be able to employ such a percentage of dispersed light with a much greater resolution.

As illustrated in FIG. 2B at least some dispersion modules 200 according to the present invention employ a detector 255 placed after the exit of the module. This detector 255 may be located within the module 200 or may be located in a separate module, such as shown as spectrometer 30 of FIG. 1.

Figure 3:
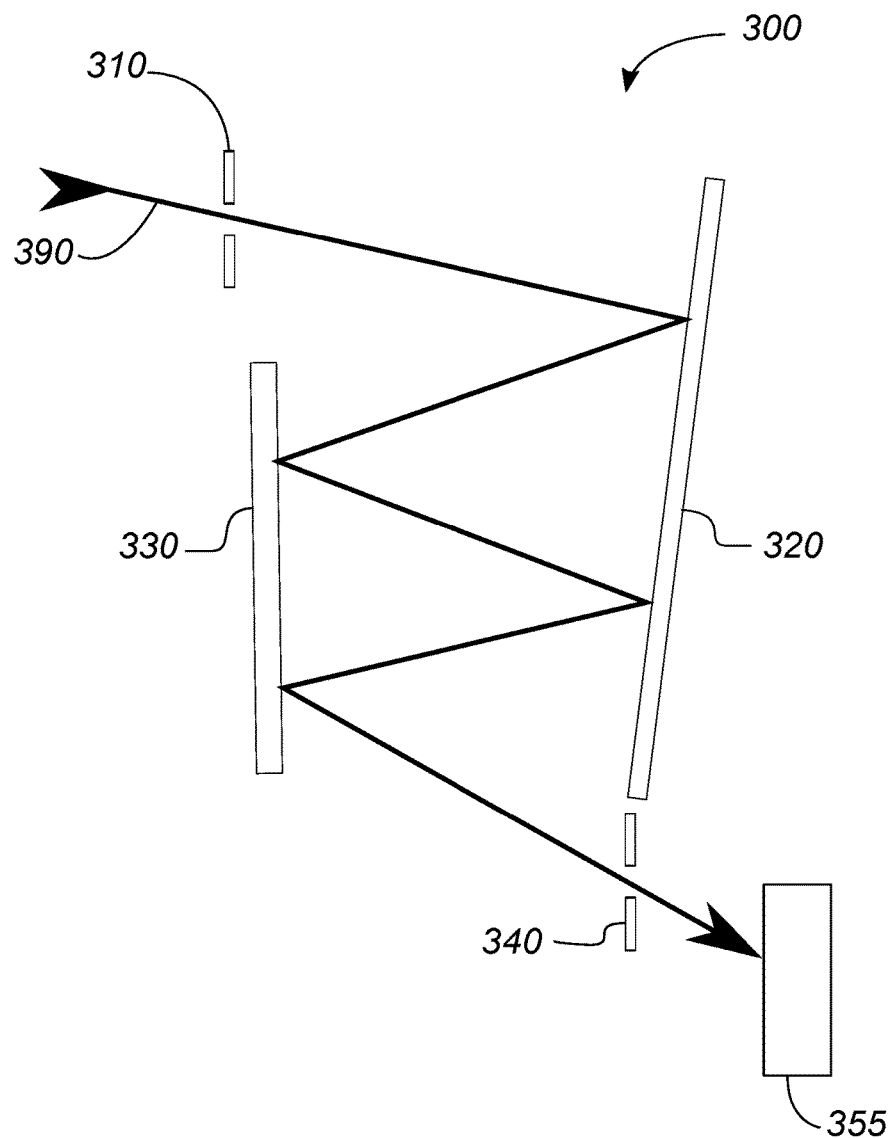
FIG. 3 illustrates another example of a dispersion module configured for a greater number of reflections and thus greater dispersion.

FIG. 3 illustrates a dispersion module 300 according to at least some embodiments of the present invention configured for a greater number of reflections and thus greater dispersion. Like reference numerals have been utilized to refer to like elements. As shown, the first 320 and second 330 dispersion gratings are spaced and angled such that light 390 (such as the plasma emitted light 24) entering the module 300 at the entrance 310 contacts both the first dispersion grating 320 and second dispersion grating 330 twice before exiting the module 200 at the exit 340. Once again there is illustrated a detector 355.

Figure 4:
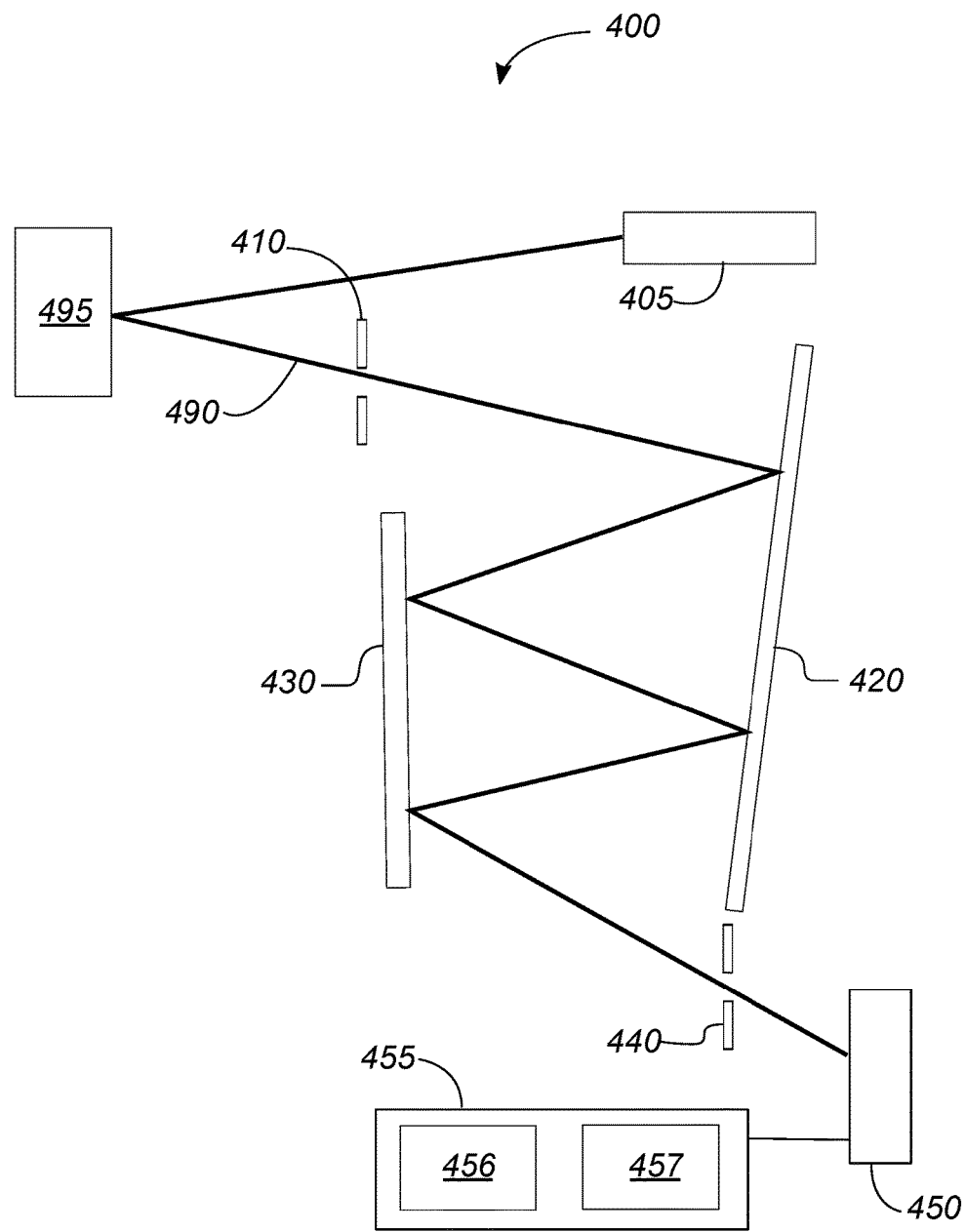
FIG. 4 illustrates another example of a dispersion module having a detector.

FIG. 4 shows a spectrometer 400 comprising a dispersion module according to the present invention. Like reference numerals have been utilized to refer to like elements. Once again the modules is comprised of a first 420 and second 430 dispersion grating, an entrance 310 for receiving light 390 and an exit 440 for transmitting it out of the module. The spectrometer 400 further comprises a detector 450 affixed within the spectrometer to detect light leaving the dispersion module.

Certain spectrometers according to the present invention have a resolution of at least 30 pm, preferably 15 pm and most preferably 10 pm due to the dispersion modules employed therein.

At least some spectrometers according to the present invention have an integrated light source 405 affixed to the spectrometer in order to provide light and thus be able to perform spectrographic analysis of a sample 495. Certain spectrometers further comprise at least one processor 456 configured to analyze information provided by the detector, and at least one memory 457 for storing instructions executable by the processor.

As illustrated above the entrance of the dispersion module may be anywhere in relation to the dispersion gratings as long as it allows light to strike the diffraction gratings at an appropriate angle. Similarly, the exit could be anywhere in relation to the gratings after the light has had a chance to contact the gratings.

Within the figures of this application, the angles are purely illustrative. The light shown is for ease of illustration and should be understood to be merely a representative of light received by the module.

As mentioned, dispersion modules according to the present invention may be employed in a wide array of applications. For example, within a LIBS application detection of various elements assists with scrap sorting and examination of welds. These applications often require detection the differences between peak wavelengths that are relatively close on the section and therefore require a greater resolution. For example, the wavelength ranges for detection of carbon are approximately 175-200 nm, within this range there are emissions for carbon at 193 nm, sulfur at 178 nm and phosphorous at 175 nm. As seen, the greater the resolution within the 25 nm bandwidth, the more accurate the spectrographic analysis. In fact, within carbon sensing applications the 193 nm wavelength emission of carbon is relatively close to an iron emission and thus complicating carbon ratio determinations. However, 10 pm resolution provides for an application where the emissions may be distinguished.

This resolution can be especially useful when determining the ratio of amplitudes between emission lines. For example, the ratio of lines between carbon and iron emissions may determine the ratio of carbon within steel and help to classify high carbon or low carbon steel. At least some dispersion modules according to the present invention are configured to assist with carbon detection as outlined above and therefore configured such that light contacts the dispersion gratings at least three times prior to exiting the module. Four or five contacts are preferred in order to provide sufficient resolution for detectors in such applications. However, three may provide sufficient resolution. Such dispersion modules provide for resolutions of at least 30 to 10 pm.

At least some dispersion modules according to the present invention find use with tunable lasers. A tunable laser may be employed so that only one absorption line is produced. That is a laser having a wavelength that would only be absorbed by one type of gas is emitted, and measurements are performed on the reflected light. Given the present invention, it would be possible to measure with enough resolution that a tunable laser is not required. The present invention would measure standard daylight with enough resolution that could be used to test fiber optic networks or other communications systems. Devices used to check telecom equipment often called Optical Spectrum Analyzers (OSA). Test equipment wavelengths.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In this description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

In an alternative embodiment, dedicated hardware implementations, such as application specific integrated circuits, programmable logic arrays, and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

Further, the methods described herein may be embodied in a computer-readable medium. The term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

As a person skilled in the art will readily appreciate, the above description is meant as an illustration of the principles of this invention. This description is not intended to limit the scope or application of this invention in that the invention is susceptible to modification, variation, and change, without departing from the spirit of this invention, as defined in the following claims.

The invention claimed is:

1. A device for analyzing a material composition of an sample via plasma spectrum analysis, the device comprising:
    a laser assembly configured to emit a beam for plasma spectrum analysis;
    an optical assembly configured to direct the beam towards a target for plasma spectrum analysis of the target;
    a dispersion module;
    the optical assembly being configured to collect a plasma emitted light emitted from a plasma and provide the plasma emitted light to the dispersion module;
    the dispersion module includes a first diffraction grating configured such that plasma emitted light from the optical assembly is diffracted by the first diffraction grating;
    the dispersion module includes a second diffraction grating such that light diffracted by the first diffraction grating would also be diffracted by the second diffraction grating; and
    wherein the dispersion module is configured to transmit light out of the dispersion module after it has been diffracted by the first and second diffraction gratings;
    wherein the first diffraction grating and second diffraction grating are positioned within the dispersion module such that light received from the optical assembly contacts the first diffraction grating at least two times before being directed out of the dispersion module; and
    a housing, the housing substantially enclosing the laser assembly, the optical assembly, and the dispersion module.

2. The device of claim 1 wherein the first diffraction grating and second diffraction grating are reflective diffraction gratings.

3. The device of claim 1, wherein the first diffraction grating and second diffraction grating are movably affixed within the dispersion module to provide for tuning of the dispersion module.

4. The device of claim 1, wherein the dispersion module has an overall dispersion rating of 20 mrad/nm, preferably X mrad/nm and most preferably Y mrad/nm.

5. The device of claim 1, wherein at least one of the first diffraction grating and second diffraction grating is a transmissive diffraction grating.

6. The device of claim 1, wherein at least one of the first diffraction grating and second diffraction grating is a blazed diffraction grating.

7. The device of claim 6, wherein the blazed diffraction grating optimized for a wavelength between 150 nm and 250 nm.

8. The device of claim 7, wherein the blazed diffraction grating optimized for a wavelength between 175 nm and 200 nm.

9. The device of claim 1, further comprising a fiber adapter, the fiber adapter being configured to receive light from the dispersion module.

10. The device of claim 9, further comprising a spectrometer, spectrometer being optically coupled to the fiber adapter.

11. The device of claim 10, wherein the spectrometer includes at least one processor configured to analyze information and at least one non-transitory memory storing instructions executable by the processor.

* * * * *

UNITED STATES PATENT AND TRADEMARK OFFICE
CERTIFICATE OF CORRECTION

PATENT NO. : 10,234,396 B1
APPLICATION NO. : 16/130563
DATED : March 19, 2019
INVENTOR(S) : Scott Charles Buchter, Michael Anthony Damento and Stanislaw Piorek It is certified that error appears in the above-identified patent and that said Letters Patent is hereby corrected as shown below:

On the Title Page

Item (73) Change "RIGAKU RAMAN TECHNOLOGIES, INC." to "Rigaku Analytical Devices, Inc."

Signed and Sealed this
Twentieth Day of December, 2022

Katherine Kelly Vidal
*Director of the United States Patent and Trademark Office*